United States Patent [19]
Philibert

[11] Patent Number: 5,696,107
[45] Date of Patent: Dec. 9, 1997

[54] METHOD OF TREATING MALE STERILITY

[75] Inventor: Daniel Philibert, La Varenne Saint Hilaire, France

[73] Assignee: Roussel UCLAF, France

[21] Appl. No.: 764,142

[22] Filed: Dec. 12, 1996

[30] Foreign Application Priority Data

Dec. 13, 1996 [FR] France .................................. 95 14750

[51] Int. Cl.[6] .................................................. A61K 31/56
[52] U.S. Cl. ........................................................ 514/182
[58] Field of Search ........................................... 514/182

[56] References Cited

U.S. PATENT DOCUMENTS 5,155,045  10/1992  Cutler et al. .

FOREIGN PATENT DOCUMENTS 0676202   10/1995   France .
1-115892   5/1989   Japan .
8604236    7/1986   WIPO .
96/36230  11/1996   WIPO .

OTHER PUBLICATIONS

Biochemical Society Transactions, vol. 17, No. 4, 1989 (2 pgs.) Journal of Chemical Ecology, vol. 13, No. 4, 1987 pp. 717–731.

The Merck Index, 1989, 11th Edition, Merck & Co., Rahway, N.J. (2 pgs) Medical Science Research, vol. 15, 1987, pp. 1443–1444 KWAN et al.

Primary Examiner—Raymond Henley, III
Attorney, Agent, or Firm—Bierman, Muserlian and Lucas

[57] ABSTRACT

A method of treating male sterility linked to insufficient fertilizing power of the spermatozoa in warm-blooded animals comprising administering to warm-blooded animals an amount of a compound of formula I or its acid addition salts sufficient to increase the fertilizing power of spermatozoa.

1 Claim, No Drawings

METHOD OF TREATING MALE STERILITY

STATE OF THE ART

The preparation of $5\alpha$-$\Delta^{16}$-androstene-$3\alpha$-ol is described by Prelog et al in Helv. Chim. Acta, Vol 27 (1944), p. 66 and its esters can be prepared by known methods. This product is known for its pheromonal properties: Gower D. B.: Quantification of odorous $\Delta^{16}$-antrostene steroids in vertebrates and in Chemical Signals in Vertebrates, 5 (Edited by D. W. Macdonald, D. Müller-Schwarze and S. E. Natynczuk). Oxford University Press, Oxford (1990).

OBJECTS OF THE INVENTION

It is an object of the invention to provide a novel method of treating male sterility due to insufficient fertilizing power of spermatozoa and compositions therefore.

These and other objects and advantages of the invention will become obvious from the following detailed description.

THE INVENTION

The novel method of the invention for treating male sterility linked to insufficient fertilizing power of the spermatozoa in warm-blooded animals comprises administering to warm-blooded animals an amount of $5\alpha$-$\Delta^{16}$-androstene-$3\alpha$-ol or its esters sufficient to increase the fertilizing power of spermatozoa.

Examples of carboxylic acids for the preparation of the esters are aliphatic and aromatic carboxylic acids of 1 to 12 carbon atoms such as acetic acid, benzoic acid, isopropionic acid, propionic acid, butyric acid, isobutyric acid, valeric acid, isovaleric acid, oxalic acid, succinic acid, pivalic acid and undecanoic acid, preferably acetic acid.

The products of the invention have an activity vis-à-vis the influx of calcium into the spermatozoa. In fact, the results of tests show that these products act directly at the level of the membrane of the spermatozoa and stimulate the influx of calcium into the spermatozoa. The products produce an increase in intracellular calcium ($[Ca^{2+}]i$) which at $10^{-5}M$ reaches an intensity equal to that produced by progesterone (Cf. test 1). They therefore have a potential use in controlling the acrosome reaction and therefore affect the fertilizing power of the spermatozoon.

They can thus be used in the prevention and/or the treatment of certain forms of male sterility characterized by an insufficient fertilizing power of the spermatozoa. The products are particularly advantageous because they have no hormonal or anti-hormonal activity (cf Test 2) and there is no alteration at the level of spermatogenesis and above all of the libido.

These products can be used in men or women. In women, they are used solely as a pre- or post-coital local treatment. Finally, these products can also be used in the veterinary domain.

The compositions may be in the form of tablets, dragees, capsules, granules, suppositories, injectable preparations, pessaries and in particular vaginal pessaries, ointments, creams, gels, microbeads, implants and patches, which are prepared according to the usual methods.

The compounds may be administered orally, rectally, parenterally and the usual daily dose is between 0,15 to 15 mg/kg depending on the method of administration and the specific compound. The compounds may also be administered intravaginally in women.

Examples of suitable pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing and emulsifying agents or preservatives.

In the following examples, there are described several preferred embodiments to illustrate the invention. However, it should be understood that the invention is not intended to be limited to the specific embodiments.

PHARMACOLOGICAL TESTS

TEST 1: Increase in the concentration of intra-cellular calcium ($[Ca^{2+}]i$) induced by progesterone and $5\alpha$-$\Delta^{16}$-androstene-$3\alpha$-ol (product W): Comparison of the effects of progesterone at $10^{-5}M$ and of the product of the invention at $10^{-5}M$ on $[Ca^{2+}]i$

METHOD

Preparation of the Human Spermatozoa

The human sperm came from healthy donors and the mobile spermatozoa were separated by centrifugation with a Percoll gradient (47.5–95%), then resuspended in a hypertonic BWW (Biggers Whitten and Whittingghan) medium containing 166 mM of NaCl, 5 mM of KCl, 1.3 mM of $CaCl_2$, 1.2 mM of $KH_2PO_4$, 1.2 mM of $MgSO_4$, 5.5 mM of glucose, 21 mM of sodium lactate, 0.25 mM of sodium pyruvate, 25 mM of $NaHCO_3$, 20 mM of Hepes and 0.8 of HSA (Human Serum Albumin) (410 mosm/liter), pH 7.4 at ambient temperature.

Measurement of the Intracellular Calcium

The mobile spermatozoa were incubated for at least 2 hours in the BWW/HSA capacitating medium and then were incubated at a concentration of $5-10 \times 10^6$/ml with Fura2-AM (final concentration 2 µm) at 37° C. for 45 minutes. After washing by centrifugation for 10 minutes in BWW without HSA, the spermatozoa were resuspended at a concentration of $4 \times 10^6$/ml. The fluorescence signal was measured at 37° C. using a spectrofluorimeter at excitation wavelengths of 340 and 380 nm (PTIM 2001-Kontron) or at 340, 360 and 380 nm (Hitachi F 2000 - B. Braun Science Tec.). The fluorescence emission was recorded at 505 nm. Progesterone or the products to be tested, dissolved in absolute ethanol, were added to the incubation medium at a final concentration of 0.1% of ethanol. When an antagonistic effect of progesterone was sought, the product was added to the medium 2 minutes before the progesterone. At the end of each dosage, 5 µM of ionomycin were added to the sample to measure the maximum fluorescence signal and then the spermatozoa were made permeable with 0.05% of Triton X-100, and 10 mM of EGTA were added at a pH of 9.5 to measure the minimum fluorescence signal. These values allowed the intracellular calcium concentration ($[Ca^{2+}]i$) to be calculated by the method described by Grunkiewicz et al (1985) J. Biol. Chem., Vol. 260, p. 3440–3450. The results of the intracellular calcium concentrations were expressed relative to the base level arbitrarily taken to be equal to 1.

| RESULTS: | |
|---|---|
| Progesterone | Product W |
| 6.4 | 5.69 |

The results are expressed relative to the base level taken to be equal to 1 and are an average of 3 experiments. The initial base levels were of the order of 200 nm.

CONCLUSION

Effect on the Intracellular Calcium of Human Spermatozoa

Progesterone at the concentration of $10^{-5}$M induced a transitory increase in the $[Ca^{2+}]i$ followed by a second phase where the $[Ca^{2+}]i$ was slightly higher than the base level. Product W produced an increase in the $[Ca^{2+}]i$ which at $10^{-5}$M reached an intensity (88.9%±36.1%) equal to that produced by progesterone. Such a product can therefore stimulate the acrosome reaction and therefore can be used in certain forms of sterility characterized by an insufficient fertilizing power of the spermatozoa.

TEST 2: Study of the activity of the products on the hormonal receptors

METHOD

Either the natural hormonal receptor of a rat (androgen receptor AR), or the human recombinant receptor (progesterone receptor PR, glucocorticoid receptor GR, mineralocorticoid receptor MR, estrogen receptor ER) were used. The analyses methods and the calculation methods were described in or equivalent to those proposed in European Patent Application 0269 635 A1.

RESULTS

The results of the RBA (Relative Bond Affinity) were as follows:

| Receptors | Product W |
|---|---|
| Progesterone | <0.1 |
| Progesterone = 100 | |
| Glucocorticoid | <0.1 |
| Dexamethasone = 100 | |
| Mineralocorticoid | <0.1 |
| Aldosterone = 100 | |
| Estrogen | <0.1 |
| Estradiol = 100 | |
| Androgen | <0.1 |
| Testosterone = 100 | |

Product W had no affinity vis-à-vis the hormonal receptors.

Various modifications of the compositions and method of the invention may be made without departing from the spirit or scope thereof and it should be understood that the invention is intended to be limited only as defined in the appended claims.

What I claim is:

1. A method of treating male sterility linked to insufficient fertilizing power of the spermatozoa in warm-blooded animals comprising administering to warm-blooded animals an amount of $5\alpha$-$\Delta^{16}$-androstene-$3\alpha$-ol or its non-toxic, pharmaceutically acceptable esters sufficient to increase the fertilizing power of spermatozoa.

* * * * *